(12) United States Patent
Watson et al.

(10) Patent No.: US 9,927,452 B2
(45) Date of Patent: Mar. 27, 2018

(54) PIPETTING SYSTEM

(71) Applicant: R. J. REYNOLDS TOBACCO COMPANY, Winston-Salem, NC (US)

(72) Inventors: Nicholas Harrison Watson, Westfield, NC (US); Van Edward Key, Tobaccoville, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 587 days.

(21) Appl. No.: 14/464,078

(22) Filed: Aug. 20, 2014

(65) Prior Publication Data

US 2016/0054345 A1    Feb. 25, 2016

(51) Int. Cl.
| | | |
|---|---|---|
| *G01N 35/10* | (2006.01) | |
| *B01L 3/02* | (2006.01) | |
| *B65B 39/12* | (2006.01) | |
| *B65B 3/00* | (2006.01) | |

(52) U.S. Cl.
CPC ........ *G01N 35/1009* (2013.01); *B01L 3/0217* (2013.01); *B01L 3/0275* (2013.01); *B65B 3/003* (2013.01); *B65B 39/12* (2013.01); *B01L 2200/025* (2013.01); *B01L 2200/14* (2013.01); *B01L 2300/0672* (2013.01); *B01L 2300/0858* (2013.01)

(58) Field of Classification Search
CPC ................................................. G01N 35/1009
See application file for complete search history.

(56) References Cited

U.S. PATENT DOCUMENTS

| | | | |
|---|---|---|---|
| 3,707,174 A | | 12/1972 | Lewis |
| 3,855,868 A | | 12/1974 | Sudvaniemi |
| 3,991,627 A | * | 11/1976 | Laird .................. B01F 11/0008 422/50 |
| 4,713,974 A | * | 12/1987 | Stone ..................... G01N 30/24 422/64 |
| 4,875,605 A | * | 10/1989 | Weston ................ B01L 3/0217 222/402.18 |
| 5,443,792 A | | 8/1995 | Bühler |
| 5,763,278 A | | 6/1998 | Sickinger et al. |
| 6,431,015 B1 | | 8/2002 | Hodac et al. |
| 6,627,160 B2 | | 9/2003 | Wanner |
| 6,780,381 B2 | | 8/2004 | Yiu |
| 6,841,130 B2 | | 1/2005 | Lehtinen et al. |
| 7,055,723 B2 | | 6/2006 | Ingenhoven et al. |
| 7,425,311 B2 | | 9/2008 | Gfrörer et al. |
| 7,726,320 B2 | | 6/2010 | Robinson et al. |
| 7,964,160 B2 | | 6/2011 | Zuppiger et al. |
| 8,528,569 B1 | | 9/2013 | Newton |
| 8,580,197 B2 | | 11/2013 | Glauser et al. |
| 2001/0019845 A1 | | 9/2001 | Bienert et al. |
| 2001/0028864 A1 | | 10/2001 | Tyberg et al. |
| 2001/0043885 A1 | | 11/2001 | Wanner |
| 2002/0125647 A1 | * | 9/2002 | Ludwig ............... E21D 21/0086 277/317 |

(Continued)

*Primary Examiner* — Robert R Raevis
(74) *Attorney, Agent, or Firm* — Womble Bond Dickinson (US) LLP (57) ABSTRACT

The present invention provides a pipette assembly and a liquid handling element employing such a pipette assembly for filling containers. The pipette assembly comprises a biasing member that prevents the containers from being displaced vertically upon withdrawal of the pipette assembly from the containers.

33 Claims, 4 Drawing Sheets

(56) References Cited

U.S. PATENT DOCUMENTS

| | | |
|---|---|---|
| 2004/0071602 A1 | 4/2004 | Yiu |
| 2007/0134808 A1* | 6/2007 | Sullivan ................ B01L 3/0293 436/180 |
| 2008/0105710 A1* | 5/2008 | Yu ............................ B05C 5/02 222/160 |
| 2009/0065532 A1* | 3/2009 | Lafond ................ B05C 17/015 222/389 |
| 2011/0183407 A1 | 7/2011 | Pihl et al. |
| 2012/0199118 A1 | 8/2012 | Cuzydlo |
| 2013/0047751 A1 | 2/2013 | Voss et al. |
| 2014/0000638 A1 | 1/2014 | Sebastian et al. |
| 2014/0004930 A1 | 1/2014 | Cannon et al. |
| 2014/0060555 A1 | 3/2014 | Chang et al. |
| 2014/0112839 A1 | 4/2014 | Richardson |
| 2014/0199779 A1 | 7/2014 | Yasui et al. |
| 2014/0209105 A1 | 7/2014 | Sears et al. |
| 2014/0261408 A1 | 9/2014 | DePiano et al. |
| 2014/0261487 A1 | 9/2014 | Chapman et al. |
| 2015/0216232 A1 | 8/2015 | Bless et al. |
| 2015/0335071 A1 | 11/2015 | Brinkley et al. |

* cited by examiner

PIPETTING SYSTEM

FIELD OF THE INVENTION

The present invention relates primarily to a pipetting apparatus, which provides for dispensing of one or more liquids into containers.

BACKGROUND OF THE INVENTION

Dispensing relatively small volumes of liquids into individual containers in a precise and repeatable manner is desirable for a wide range of applications. Various types of liquid handling instruments can be used for such purposes, which range from simple hand-held devices to large-scale, automated pipetting apparatus.

Typically, the liquid to be dispensed is introduced from a reservoir into one or a series of pipettes, which pipettes comprise an elongated chamber configured at the proximal end to accept the liquid to be dispensed and having a tip at the distal end with a passageway formed therethrough. Accordingly, the liquid passes from a reservoir through the pipettes and can be released through the tip at the distal end thereof. In some embodiments, the liquid can be released directly through the tip into the desired container. In some embodiments, the tip is equipped with a secondary delivery mechanism, e.g., a cannula or needle.

In recent years, there have been proposed numerous smoking products, flavor generators and medicinal inhalers that utilize electrical energy to heat and vaporize volatile materials, or otherwise attempt to provide many of the sensations of smoking, without burning tobacco to any significant degree. See, for example, the various types of aerosol generation devices described, discussed, or referenced in U.S. Pat. No. 7,726,320 to Robinson et al., U.S. patent application Ser. No. 13/826,929, filed Mar. 14, 2013, to Ampolini et al., Ser. No. 14/011,992, filed Aug. 28, 2013, to Davis et al., and Ser. No. 14/170,838, filed Feb. 3, 2014, to Bless et al.; which are incorporated herein by reference in their entireties.

In this regard, certain tobacco products that have employed electrical energy to produce heat for smoke or aerosol formation, and in particular, certain products that have been referred to as electronic cigarette products, have become commercially available throughout the world. Representative products that resemble many of the attributes of traditional types of cigarettes, cigars or pipes have been marketed as ACCORD® by Philip Morris Incorporated; ALPHA™, JOYE 510® and M4™ by InnoVapor LLC; CIRRUS™ and FLING™ by White Cloud Cigarettes; BLU™ by Lorillard Technologies, Inc.; COHITA™, COLIBRI™, ELITE CLASSIC™, MAGNUM™, PHANTOM™ and SENSE™ by Epuffer® International Inc.; DUOPRO™, STORM™ and VAPORKING® by Electronic Cigarettes, Inc.; EGAR™ by Egar Australia; eGo-C™ and eGo-T™ by Joyetech; ELUSION™ by Elusion UK Ltd; EONSMOKE® by Eonsmoke LLC; FIN™ by FIN Branding Group, LLC; SMOKE® by Green Smoke Inc. USA; GREENARETTE™ by Greenarette LLC; HALLIGAN™, HENDU™, JET™, MAXXQ™, PINK™ and PITBULL™ by Smoke Stik®; HEATBAR™ by Philip Morris International, Inc.; HYDRO IMPERIAL™ and LXE™ from Crown7; LOGIC™ and THE CUBAN™ by LOGIC Technology; LUCI® by Luciano Smokes Inc.; METRO® by Nicotek, LLC; NJOY® and ONEJOY™ by Sottera, Inc.; NO. 7™ by SS Choice LLC; PREMIUM ELECTRONIC CIGARETTE™ by PremiumEstore LLC; RAPP E-MYSTICK™ by Ruyan America, Inc.; RED DRAGON™ by Red Dragon Products, LLC; RUYAN® by Ruyan Group (Holdings) Ltd.; SF® by Smoker Friendly International, LLC; GREEN SMART SMOKER® by The Smart Smoking Electronic Cigarette Company Ltd.; SMOKE ASSIST® by Coastline Products LLC; SMOKING EVERYWHERE® by Smoking Everywhere, Inc.; V2CIGS™ by VMR Products LLC; VAPOR NINE™ by VaporNine LLC; VAPOR4LIFE® by Vapor 4 Life, Inc.; VEPPO™ by E-CigaretteDirect, LLC; VUSE® by R. J. Reynolds Vapor Company; Mistic Menthol product by Mistic Ecigs; and the Vype product by CN Creative Ltd. Yet other electrically powered aerosol delivery devices, and in particular those devices that have been characterized as so-called electronic cigarettes, have been marketed under the tradenames COOLER VISIONS™; DIRECT E-CIG™; DRAGONFLY™; EMIST™; EVERSMOKE™; GAMUCCI®; HYBRID FLAME™; KNIGHT STICKS™; ROYAL BLUES™; SMOKETIP®; SOUTH BEACH SMOKE™.

Additional manufacturers, designers, and/or assignees of components and related technologies that may be employed in aerosol delivery device include Shenzhen Jieshibo Technology of Shenzhen, China; Shenzhen First Union Technology of Shenzhen City, China; Safe Cig of Los Angeles, Calif.; Janty Asia Company of the Philippines; Joyetech Changzhou Electronics of Shenzhen, China; SIS Resources; B2B International Holdings of Dover, Del.; Evolv LLC of OH; Montrade of Bologna, Italy; Shenzhen Bauway Technology of Shenzhen, China; Global Vapor Trademarks Inc. of Pompano Beach, Fla.; Vapor Corp. of Fort Lauderdale, Fla.; Nemtra GMBH of Raschau-Markersbach, Germany, Perrigo L. Co. of Allegan, Mich.; Needs Co., Ltd.; Smokefree Innotec of Las Vegas, Nev.; McNeil AB of Helsingborg, Sweden; Chong Corp; Alexza Pharmaceuticals of Mountain View, Calif.; BLEC, LLC of Charlotte, N.C.; Gaitrend Sarl of Rohrbach-lès-Bitche, France; FeelLife Bioscience International of Shenzhen, China; Vishay Electronic BMGH of Selb, Germany; Shenzhen Smaco Technology Ltd. of Shenzhen, China; Vapor Systems International of Boca Raton, Fla.; Exonoid Medical Devices of Israel; Shenzhen Nowotech Electronic of Shenzhen, China; Minilogic Device Corporation of Hong Kong, China; Shenzhen Kontle Electronics of Shenzhen, China, and Fuma International, LLC of Medina, Ohio, and 21st Century Smoke of Beloit, Wis.

Such aerosol delivery devices generally comprise a cartridge in which aerosolizable components are contained. These cartridges are advantageously filled with the aerosolizable components in an automated manner. However, challenges associated with the automated filling of certain cartridges and other containers that already contain one or more other components, as will be described in greater detail herein, limit the use of traditional liquid handling instruments. Accordingly, modifications to automated instruments to allow for the filling of certain types of cartridges and other containers while avoiding such challenges would be desirable.

SUMMARY OF THE INVENTION

The present invention provides a pipette assembly and a liquid handling element employing such a pipette assembly for filling containers. The pipette assembly comprises a biasing member (e.g., spring element) that prevents the containers from being displaced vertically upon withdrawal of the assembly from the containers.

In one aspect of the disclosure, a pipette assembly, comprising a chamber having an elongated body capable of holding a liquid, wherein the chamber comprises a proximal end for input of the liquid and an opposing distal end in fluid communication with a cannula for dispensing of the liquid into a container, further comprising a biasing member surrounding and associated with at least a portion of the pipette assembly is provided.

In some embodiments, the biasing member is temporarily or permanently attached to the pipette assembly. The biasing member can, in certain embodiments, the biasing member comprises a helical spring. The makeup of the biasing member can vary and, in some embodiments, the biasing member (e.g., helical spring) may comprise stainless steel. In some embodiments, the compression force of the biasing member is between about 2.1 g and about 2.5 g. The biasing member can optionally further comprise a restraining component on the bottom end thereof, which modifies the diameter of the bottom end of the biasing member (e.g., wherein the restraining component is a metal washer).

In an additional aspect of the disclosure, a method for dispensing a liquid into a container is provided, comprising: providing a moveable liquid handling arm comprising at least one pipette assembly and a controller to which the liquid handling arm is electrically connected, wherein the at least one pipette assembly comprises a chamber having an elongated body capable of holding a liquid, wherein the chamber comprises a proximal end for input of the liquid and an opposing distal end in fluid communication with a cannula for dispensing of the liquid into a container, further comprising a biasing member surrounding and associated with at least a portion of the pipette assembly, providing one or more containers to be filled; positioning the moveable liquid handling arm horizontally such that one container is vertically below each pipette assembly; lowering the pipette assembly vertically such that the cannula of the pipette assembly is within the container, wherein the biasing member engages the top of the container and is compressed; dispensing the liquid into the container; and withdrawing the pipette assembly from the container, wherein the biasing member prevents the container from being vertically displaced during upwards withdrawal of the pipette assembly from the container.

In some embodiments, the containers comprise a solid or semi-solid material and the compression force of the biasing member is at least that required for the cannula to penetrate said solid or semi-solid material. The solid or semi-solid material may be, for example, a fibrous material including, but not limited to, a material comprising cellulose acetate.

In a still further aspect of the disclosure, a method for dispensing an aerosol precursor composition into a cartridge for an electronic smoking article comprising a fibrous reservoir is provided, the method comprising: providing a moveable liquid handling arm comprising at least one pipette assembly and a controller to which the liquid handling arm is electrically connected, wherein the at least one pipette assembly comprises a chamber having an elongated body capable of holding a liquid, wherein the chamber comprises a proximal end for input of the liquid and an opposing distal end in fluid communication with a cannula for dispensing of the liquid into the cartridge, further comprising a biasing member surrounding and associated with at least a portion of the pipette assembly, providing one or more cartridges to be filled; positioning the moveable liquid handling arm horizontally such that one cartridge is vertically below each pipette assembly; lowering the pipette assembly vertically such that the cannula of the pipette assembly contacts the fibrous reservoir within the cartridge, wherein the biasing member engages the top of the cartridge and is compressed; dispensing the liquid into the cartridge; and withdrawing the pipette assembly from the cartridge, wherein the biasing member prevents the cartridge from being vertically displaced during upwards withdrawal of the pipette assembly from the cartridge.

In certain embodiments, the method may further comprise tilting the cartridge in one or more directions with respect to the vertical plane prior to the dispensing step. For example, the method can further comprise tilting the cartridge prior to the dispensing step such that the cartridge is at an angle of between about 5 and 45 degrees with respect to the vertical plane and the liquid is dispensed, e.g., down an inner surface (e.g., wall(s)) of the cartridge. During the dispensing step, in some embodiments, the cannula is in contact with one or both of the fibrous reservoir and the cartridge. The associated compression force of the biasing member in such situations is typically at least that required for the cannula to overcome the friction associated with the contact with one or both of the fibrous reservoir and the cartridge.

BRIEF DESCRIPTION OF THE DRAWINGS

In order to provide an understanding of embodiments of the invention, reference is made to the appended drawings, which are not necessarily drawn to scale, and in which reference numerals refer to components of exemplary embodiments of the invention. The drawings are exemplary only, and should not be construed as limiting the invention.

DETAILED DESCRIPTION OF THE PREFERRED EMBODIMENTS

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art. As used in this specification and the claims, the singular forms "a," "an," and "the" include plural referents unless the context clearly dictates otherwise. Reference to "dry weight percent" or "dry weight basis" refers to weight on the basis of dry ingredients (i.e., all ingredients except water).

Generally, the invention provides a pipette assembly for dispensing a liquid into a container. The invention further provides a liquid handling instrument for dispensing one or more liquids into containers through a plurality of delivery devices (e.g., including one or more of the pipette assemblies described herein). In particular, the invention provides a mechanism associated with such an instrument that serves as a restraint for the vertical upward displacement of the containers upon withdrawal of the delivery devices from the containers after dispensing the liquid therein. Advantageously, such mechanisms can be associated with the liquid handling arm of an instrument such that the mechanism travels with the liquid handling arm (e.g., as it moves in the vertical and/or horizontal plane to dispense liquid into a subsequent set of containers).

The mechanism to serve as a restraint for the displacement of the containers is typically a biasing member. A biasing member is understood to be any resilient component capable of maintaining a force between contacting surfaces and/or storing and releasing energy. In some embodiments, the biasing member may be an elastic unit, generally understood to be a material that is capable of resuming its normal shape after contraction/compression or extension/stretching (e.g., including, but not limited to, a material comprising natural or synthetic rubber, silicone, or other elastic or viscoelastic material). In some embodiments, the biasing member may be a spring, such as a compression spring. In typical embodiments, when no portion of the pipette assembly described herein is in contact with a container to be filled, the biasing member is generally in an uncompressed state. However, upon contact between the biasing member and the container to be filled, the biasing member typically undergoes compression. The biasing member can apply a temporary biasing force between the pipette assembly and the top of the container to prevent the upward movement of the container upon removal of the pipette assembly from the container. For ease of reference, the embodiments described herein will be described as comprising a "spring element," although it is understood that any type of biasing member could be used.

Figure 1:
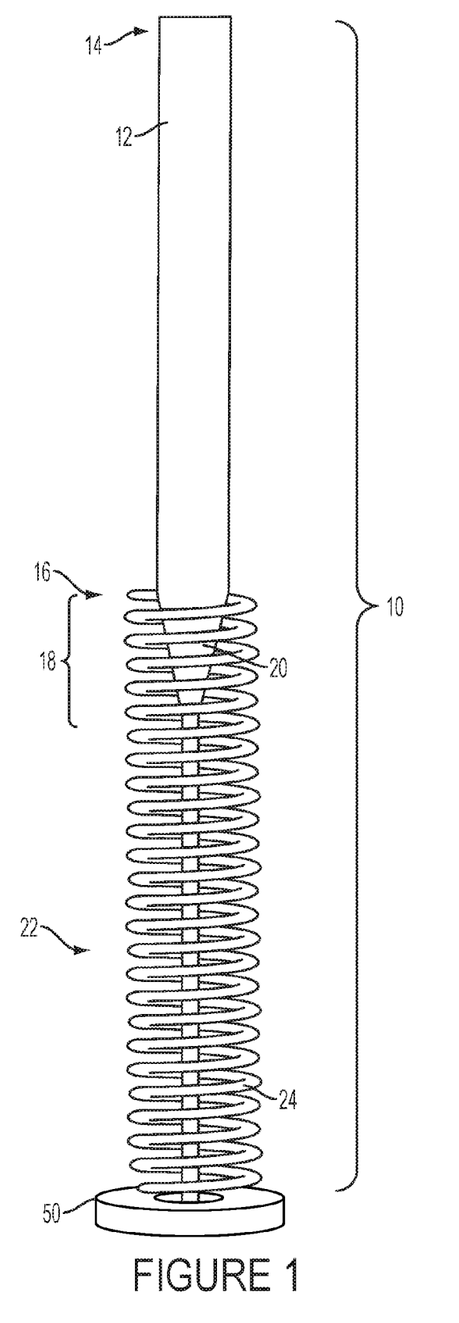
FIG. 1 is a schematic drawing of a pipette assembly 10 comprising a biasing element 24 as described herein.

In accordance with a first embodiment, as schematically presented in FIG. 1, a pipette assembly 10 is provided, which comprises a chamber 12 having an elongated body capable of holding and dispensing a liquid. Chamber 12 has an open proximal end 14 and an opposing distal end 16 that has a tapered tip 18 with a passageway 20 formed therethrough. One end of passageway 20 opens into chamber 12 to provide communication between the tip 18 and the chamber 12 and the opposing end of passageway 20 is open, such that liquid can pass therethrough and be dispensed through a cannula 22 that is coupled to tip 18. A biasing member 24 is provided, which is adapted such that one (top) end of the spring element is situated around the diameter of pipette assembly 10 (e.g., around tip 18, as illustrated), encircling the diameter of the pipette assembly, and extending vertically downward.

In some embodiments, the top of the spring element is vertically aligned with or below the intersection of the distal end 16 of chamber 12 and the tip 18. For example, in some embodiments, spring element 24 has a diameter at the top (i.e., at the position situated around the diameter of the tip 18) that is equal to or smaller than the diameter of the chamber 12, such that the diameter of the spring at the top is equal to the diameter of some portion of the tapered tip 18. In some embodiments, the intersection of the distal end 16 of chamber 12 and the tip 18 is functionalized with a restraining mechanism (e.g., a raised line or groove around the circumference of the intersection) to prevent the top of spring element 24 from extending above the intersection.

However, the present disclosure is not limited thereto and, in certain embodiments, the top of the spring element 24 may be associated with the pipette assembly in another fashion. For example, it may encircle the diameter of the chamber 12 at any position thereon, including at the top thereof (e.g., at or close to open proximal end 14). As another example, chamber 12 can comprise a raised feature at or near the distal end 16 that renders the diameter of the chamber at that raised position greater than that of the diameter at the top of the spring. In still other embodiments, either the chamber 12 or the tip 18 comprises a groove or other structure within which the top of the spring can sit. Consequently, in such embodiments, when the pipette assembly 10 is equipped with a spring element 24, the top of the spring will not be vertically displaced when the spring is compressed upwards under typical forces.

The top of the spring may be attached or unattached to the point at which it contacts the remainder of the pipette assembly. Any method for attachment can be used to associate the spring element 24 with the pipette assembly, including but not limited to, use of an adhesive or fastener associated with the spring element and/or the pipette assembly. Advantageously, in some embodiments, the spring element can be press fit to the pipette-to-instrument fitting. Although not limited thereto, the top of spring 10 is advantageously (temporarily or permanently) affixed or connected to the pipette assembly in some fashion such that, when the bottom of cannula 22 is not resting on a surface, the spring 10 remains associated with the pipette assembly (and does not slide off the pipette assembly when held in position vertically).

The length of the spring element associated with the pipette assembly in uncompressed form can vary and can be dependent upon the point of contact between the pipette assembly and the top of the spring. The length is also dependent on the depth of the container to be filled using the pipette assembly. One important feature in preferred embodiments is that, regardless of the spring length, the bottom end of the uncompressed spring is generally horizontally disposed at some position along the length of cannula 22. The position of the bottom end of the uncompressed spring in combination with the compressibility of the spring is an important consideration for the function of the pipette assembly in the context of a large-scale automated instrument.

The bottom end of spring element 24 is vertically displaceable by vertical compression of the spring upwards when the bottom end of spring element 24 comes into contact with resistance. The bottom of the spring, in certain embodiments, is designed to come into contact with resistance at the top surface of the container into which liquid is to be dispensed. Accordingly, when the pipette assembly is employed, the cannula 22 extends into the container; spring element 24 engages the top diameter of the container, becoming compressed as the pipette assembly is moved vertically downwards. In order to engage the top diameter of the container, the diameter of the bottom of the spring element that comes into contact with the container must be sized such that the inner diameter of the spring element is comparable to that that of the container to ensure that the spring rests on top of the container, resulting in compression of the spring upwards when the spring element contacts the container. The bottom of spring element 24 may, in some embodiments, be modified through the addition of a restraining component. The restraining component can be any element affixed to the bottom of the spring element that changes the inner and/or outer diameter of the bottom end of the spring element. In one particular embodiment, the restraining component is a washer of a particular diameter attached to the bottom of the spring, where the inner diameter of washer chosen to ensure washer-to-container engagement. Although the restraining component can be roughly circular, it is noted that other shapes can be employed to serve the desired function (e.g., rectangular, square, triangular, oval, etc.), so long as the dimensions of the restraining component are such that component-to-container engagement is achieved and the spring element is prevented from entering or surrounding the diameter of the container to be filled.

The makeup of the spring element itself can vary. Generally, any spring meeting the requirements described herein can be used. Springs are generally metal (e.g., stainless steel), although other materials can be used in place of or in combination with the metal. Springs are typically cylindrically shaped and are commonly composed of a single wire wrapped in a helical and/or coiled fashion. The composition of the spring as well as the thickness and number of coils, among other parameters, can be modified to achieve a desired spring constant. The spring constant, in combination with the length to which the spring is compressed, provides the force of the spring (according to Hooke's law, which states that the force needed to extend or compress a spring by a distance X is equivalent to kX, where k is the "spring constant"). The force for a given application as described herein is that at least that force needed to overcome the friction encountered by the cannula in the container to be filled. Generally, the force of the spring exceeds the friction force encountered by the cannula in the container to be filled and can be, for example, between about 2.1 g and about 2.5 g in certain embodiments. It is understood that the desired force can be achieved by tailoring one or both of the distance travelled by the spring upon compression and the spring constant (e.g., by changing the composition, number of coils, or thickness of the spring or by changing the vertical position of the end of spring 24 on the pipette assembly relative to the cannula) to achieve the goals stated herein.

Spring elements as used herein are of sufficient diameter to encircle the pipette assembly. Advantageously, in some embodiments, the diameter of the spring can be chosen such that the spring can be press fit to the pipette-to-instrument fitting. The diameter of the spring can, in some embodiments, be consistent or may be variable down the length of the spring (e.g., with smaller or larger top and/or bottom end).

Accordingly, the present disclosure also provides an automated liquid handling instrument comprising one or more pipette assemblies comprising a spring mechanism as detailed above. Various liquid handling instruments are known and can be modified by the incorporation of a spring element as described herein. A schematic representation of one such instrument 30 is provided in FIG. 2, wherein the pipette assemblies 10 of the instrument can be modified by the association of a spring element therewith as described in the present disclosure. In certain preferred embodiments, such instruments comprise an essentially horizontally oriented work surface 34 for the placement of containers; a liquid handling arm 32, equipped with at least one pipette assembly 10 for aspirating and dispensing a liquid (including at least one pipette modified as described herein); and a controller 36 to which the liquid handling arm is electrically connected, which controls operation of the instrument, including movement of the liquid handling arm and dispensing of liquid through the pipette assemblies.

The number of pipette assemblies can vary. For example, in certain embodiments, instruments are provided that comprise, e.g., four, six, eight, ten, or twelve aligned pipette assemblies in a single line. In other embodiments, the liquid handling arm is equipped with a two-dimensional arrangement of pipette assemblies (e.g., in a 4×4 arrangement, 4×8 arrangement, 10×10 arrangement, 8×8 arrangement, 8×12 arrangement or 12×12 arrangement). In certain embodiments, the containers into which liquid is to be dispensed are the wells of microtiter trays or are containers that are held in trays such as those having 96 wells (e.g., arranged as an 8×12 grid) or 384 wells (e.g., arranged as a 16×24 grid).

Of course, larger and smaller systems are also contemplated and any instrument comprising any number and arrangement of pipette assemblies can be modified to associate biasing members therewith as described herein. Exemplary instruments include, but are not limited to, those disclosed in U.S. Pat. No. 3,855,868 to Sudvaniemi; U.S. Pat. No. 5,443,792 to Buhler; U.S. Pat. No. 5,763,278 to Sickinger et al.; U.S. Pat. No. 6,627,160 to Wanner; U.S. Pat. No. 6,780,381 to Yiu; U.S. Pat. No. 6,841,130 to Lehtinen et al.; U.S. Pat. No. 7,055,723 to Ingenhoven et al.; U.S. Pat. No. 7,964,160 to Zuppiger et al.; U.S. Pat. No. 8,580,197 to Glauser et al., which are all incorporated by reference in their entireties. The instruments described herein can be used for filling a wide range of containers with a wide range of liquids (e.g., including, but not limited to, pharmaceutical solutions, liquids for analytical analysis, and aerosol forming precursors for electronic smoking articles, etc.). In some embodiments, the instruments described herein can be employed within an automated manufacturing system together with one or more other instruments, e.g., as described in U.S. patent application Ser. No. 14/227,159 to Ampolini et al., which is incorporated herein by reference.

Figure 2:
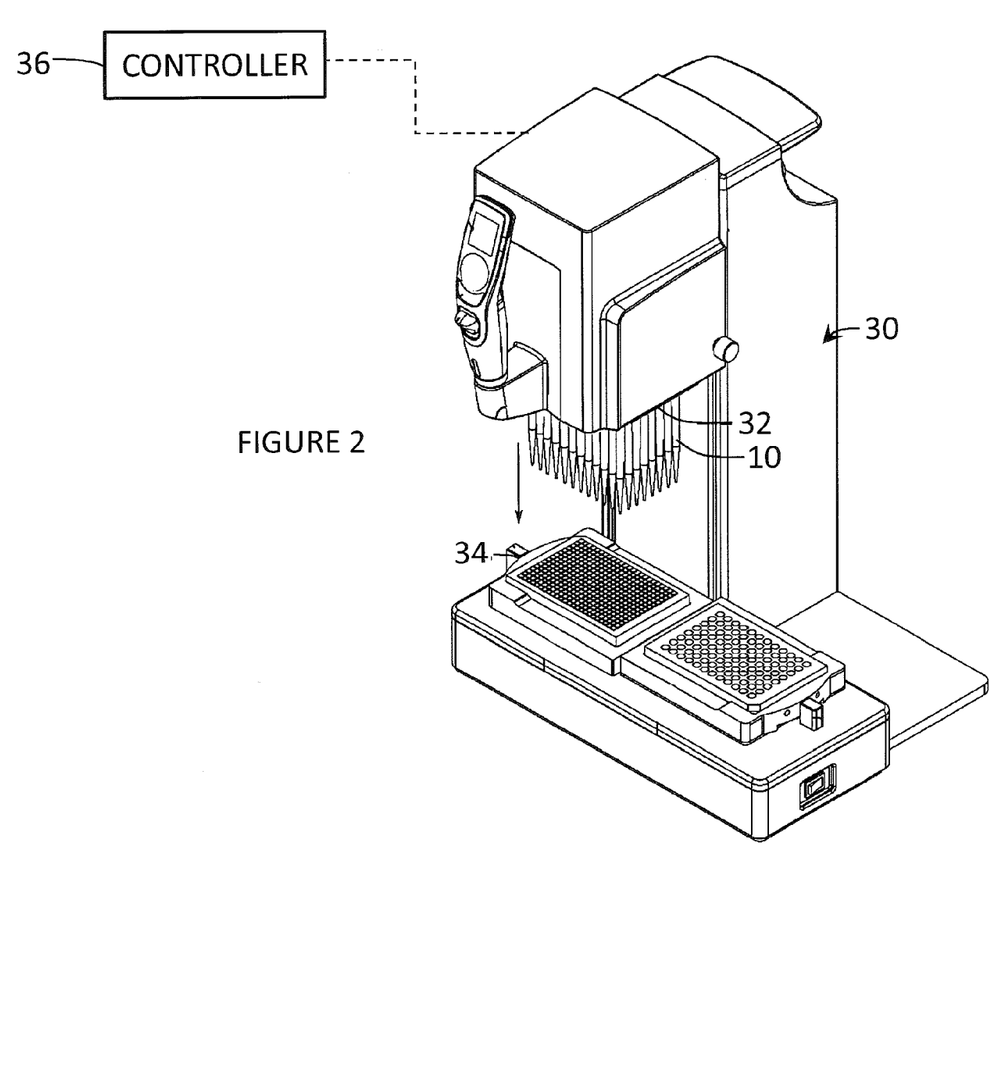
FIG. 2 is a schematic drawing of an automated liquid handling instrument 30 comprising one or more pipette assemblies.

Generally, in use, the liquid handling arm of a liquid handling instrument can iteratively dispense liquid from a series of pipette assemblies into one or more containers directly below (which can be, e.g., in aligned rows to correspond with the placement of the pipette assemblies on the liquid handling arm as shown in FIG. 2). A schematic representation of typical method steps associated with use of a liquid handling instrument comprising pipette assemblies as described herein is provided in FIG. 3. The method of use typically requires the step of providing one or more containers to be filled 40. Containers to be filled can vary in size and shape can comprise, for example, various types of vials, test tubes, cuvettes, wells, and cartridges.

Figure 3:
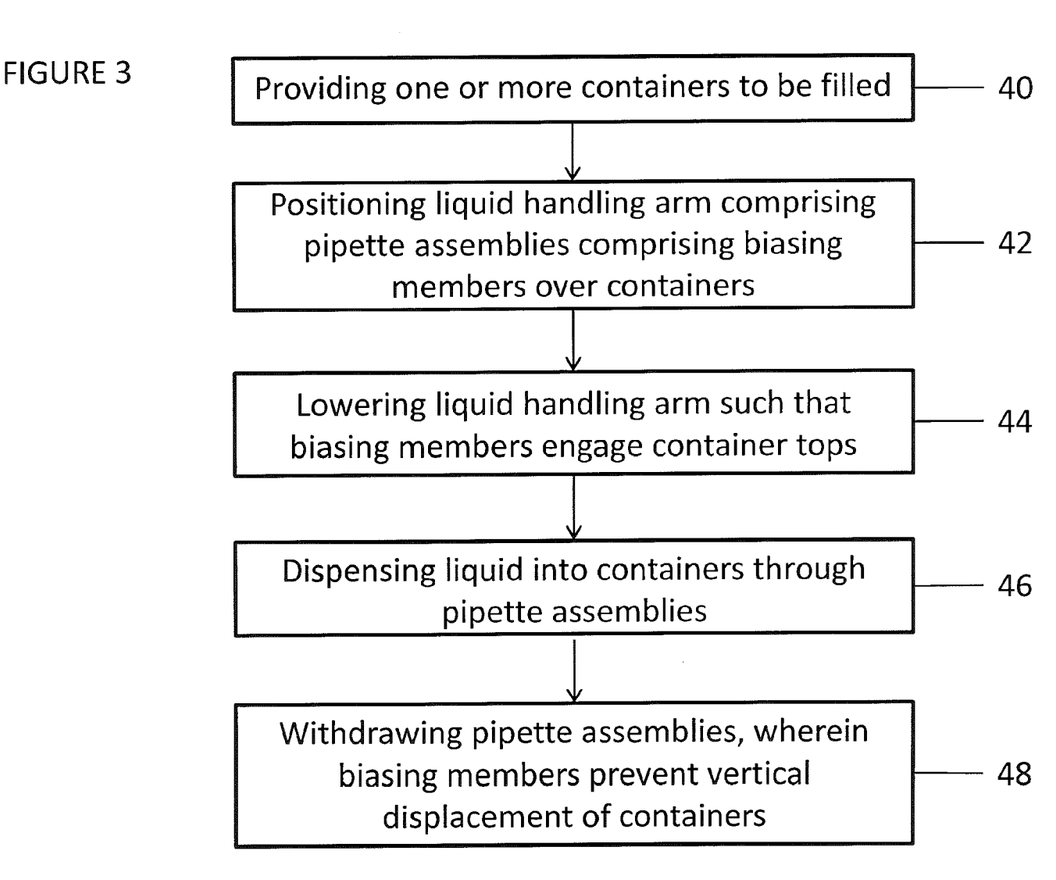
FIG. 3 is a schematic representation of the method steps of one embodiment of the present disclosure.

The liquid handling arm is positioned horizontally (e.g., in the X and Y direction) 42 such that the pipette assemblies associated therewith are aligned over the containers to be filled. The liquid handling arm then is lowered vertically downward 44 such that at least a portion of cannula 22 is within the container to be filled. Liquid is dispensed 46 into each container through the pipette assemblies. The liquid handling arm is then moved vertically upwards, such that the pipette assemblies are withdrawn vertically upwards from the containers 48. Depending upon the number of pipette assemblies associated with the liquid handling arm and the number of containers to be filled, the liquid handling arm then can optionally move horizontally to dispense liquid into a second plurality of containers directly below. These steps can be repeated until the desired number of containers on the work surface 34 are filled.

Advantageously, the spring element associated with the pipette assemblies described herein remains associated with the pipette assembly and moves vertically with the handling arm, such that bottom end of spring element 24 (or a restraining component associated therewith) comes into contact with the containers prior to the dispensing of liquid into the containers. When the bottom end of spring element 24 comes into contact with the container, any further vertical downward movement of the liquid handling arm (to ensure the cannula end is at the desired level within the container for dispensing of the liquid) results in compression of spring element 24 upwards toward the liquid handling arm.

Although any types of containers can be filled using the pipette assemblies and liquid handling instruments described herein, in certain embodiments, the pipette assemblies provided according to the present disclosure are particularly beneficial in filing containers comprising one or more solid or semi-solid materials, such as reservoir-containing cartridges, as will be described in greater detail below. Where the containers to be filled comprise a solid or semi-solid material, the cannula used to fill the container generally experiences some friction when it comes into contact with that material, which must be overcome to dispense the liquid and to withdraw the cannula 22 from the container. As the cannula is withdrawn from the container, the end of spring element 24 (or the restraining component associated therewith) remains engaged with the top diameter of the container, such that the containers are not displaced vertically upwards upon withdrawal of the cannula. Such pipette assemblies can be applicable with regard to both top down and bottom up dispensing of the liquid.

Figure 4:
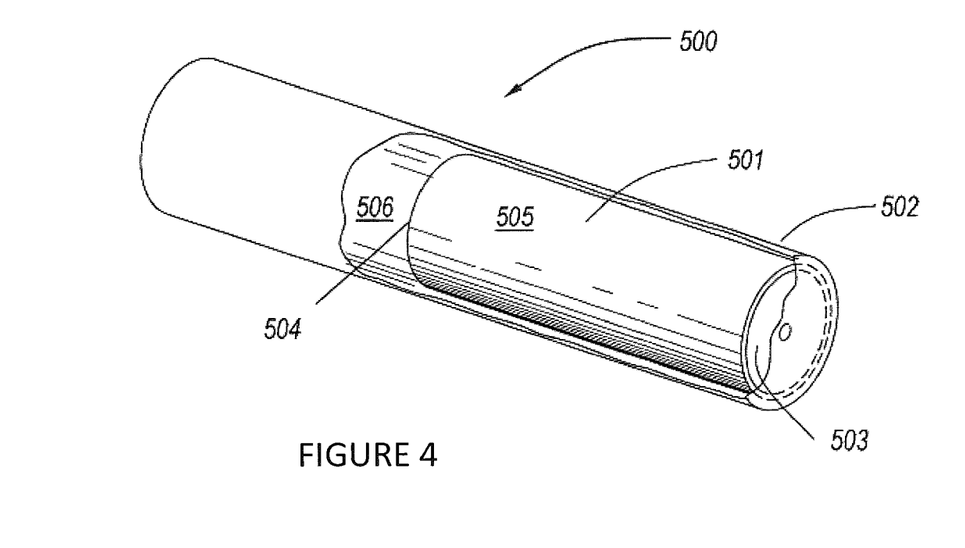
FIG. 4 provides a cut-away view of a cartridge 500 for an electronic smoking article, which can be filled using the automated liquid handling instruments described herein.

In some embodiments, the containers are cartridges to be employed within aerosol-generating devices, such as electronic smoking articles. As used herein, the term "cartridge" refers to a container, receptacle or chamber for holding, storing, or retaining a product such as a liquid, fluid, or aerosol. Certain such cartridges are described in U.S. patent application Ser. No. 14/286,552 to Brinkley et al. and Ser. No. 13,841,233 to DePiano et al., U.S. Pat. App. Pub. Nos. 2014/0060555 to Chang et al. and 2014/0000638 to Sebastian et al., and U.S. Pat. No. 7,726,320 to Robinson et al., which are all incorporated herein by reference. For example, FIG. 4 provides a cut-away view of a cartridge 500 that can be included in an electronic smoking article, including a reservoir 501. The reservoir 501 may advantageously have a diameter such that the exterior surface 505 of the reservoir can be adapted to fit within and conform to an interior surface 506 of cartridge walls 502. The reservoir is designed to retain a liquid, fluid, or aerosol within the cartridge walls 502 (e.g., wherein an aerosol precursor composition can be sorptively retained by the reservoir layer 501). The reservoir layer 501 can be in fluid connection with a transport element that can transport an aerosol precursor composition stored in the reservoir layer 501 via capillary action to an aerosolization zone.

The reservoir 501 can be e.g., fibrous and can comprise, in some embodiments, cellulose acetate. If desired, the reservoir can comprise a binder. Fillers (e.g., cellulose) and fibers formed of different materials also can be used. The reservoir can comprise about 70% to about 99% by weight cellulose acetate fibers, and the weights noted herein are measured on a dry weight basis. More specifically, the reservoir can comprise about 75% to about 98%, about 80% to about 97.5%, or about 90% to about 97% by weight cellulose acetate fibers. The reservoir can comprise about 1% to about 30% by weight of the binder. More specifically, the reservoir can comprise about 2% to about 25%, about 2.5% to about 20%, or about 3% to about 10% by weight of the binder. In specific embodiments, a reservoir according to the disclosure can comprise about 95% to about 97% by weight cellulose acetate fiber and about 3% to about 5% by weight binder. In other specific embodiments, a reservoir according to the disclosure can comprise about 80% to about 85% by weight cellulose acetate fiber and about 15% to about 20% by weight binder. A binder is understood to be a material that imparts a cohesive effect to the fibers used in forming the disclosed reservoirs. For example, the binder can be a material that partially solubilizes the cellulose acetate fibers such that the fibers bind to each other or to further fibrous materials included in the woven or nonwoven reservoir. Exemplary binders that can be used include polyvinyl acetate (PVA) binders, starch, and triacetin. Further features of cartridges including reservoirs and smoking articles implanting such cartridges can be found, for example, in U.S. patent application Ser. No. 13/802,950 to Chapman et al., filed on Mar. 14, 2014, which is incorporated herein by reference in its entirety.

Representative types of substrates, reservoirs or other components that may be employed in cartridges for supporting an aerosol precursor are described in U.S. Pat. No. 8,528,569 to Newton; and U.S. patent application Ser. No. 13/802,950, filed Mar. 15, 2013, to Chapman et al.; Ser. No. 14/011,192, filed Aug. 28, 2013, to Davis et al. and Ser. No. 14/170,838, filed Feb. 3, 2014, to Bless et al.; which are incorporated herein by reference. Additionally, various wicking materials, and the configuration and operation of those wicking materials within certain types of electronic cigarettes, are set forth in U.S. patent application Ser. No. 13/754,324, filed Jan. 30, 2013, to Sears et al.; which is incorporated herein by reference.

In such embodiments, having one or more solid or semi-solid materials contained in the cartridge and at least one such material to serve as a reservoir, the pipette assemblies described herein can extend into the reservoir material and dispense an aerosol precursor composition (e.g., commonly a liquid capable of yielding an aerosol upon application of sufficient heat, such as ingredients commonly referred to as "smoke juice," "e-liquid" and "e-juice") within the cartridge, such that at least a portion of the composition can be sorptively retained by the reservoir. The biasing member described herein allows the cannula 22 to penetrate the reservoir material and yet be effectively withdrawn therefrom following dispensing, with little to no vertical displacement of the cartridge upon the vertically upward withdrawal of the cannula.

In some embodiments, it may be advantageous to dispense liquid into cartridges or other containers that are provided at an angle with respect to cannula 22. For example, in some embodiments, a cartridge is provided that comprises a reservoir in an outer component of the cartridge. In such embodiments, it can be advantageous to modify the angle of the pipette assembly, cannula, or cartridge to be filled, such that the cannula can dispense the liquid at various angles with respect to the cartridge. In some embodiments the cannula may remain out of contact with the reservoir substrate.

In other embodiments, the cannula may contact at least a portion of the reservoir substrate and/or may contact the top, wall, or bottom of the container (e.g., the cartridge). For example, in certain embodiments, the pipette assembly can be lowered into the cartridge or container to be filled, which may be initially aligned such that its longitudinal axis is vertical or substantially vertical. The pipette assembly can then be moved sideways (within the horizontal plane) such that a portion of the pipette assembly contacts a portion of the cartridge or container (e.g., the top lip and/or a wall of the cartridge or container), causing the longitudinal axis of the cartridge or container to be tilted with respect to the vertical plane. In some embodiments, the cartridge or container may be tilted at an angle of between about 5 and about 45 degrees with respect to the vertical plane. Following this tilting, the liquid to be dispensed can then be directed down an inner surface of the cartridge or container wall(s). In such embodiments, the spring assembly associated with the pipette assembly can serve to overcome friction associated with penetration of the reservoir substrate and/or friction associated with contact between the cannula and the cartridge itself (e.g., a wall of the cartridge).

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed:

1. A pipette assembly, comprising an elongated body capable of holding a liquid, wherein the elongated body comprises a proximal end for input of the liquid and an opposing distal end in fluid communication with a cannula for dispensing of the liquid into a container, further comprising a biasing member surrounding and associated with at least a portion of the pipette assembly, wherein the biasing member is arranged such that the top of the biasing member is vertically aligned with or below the distal end of the elongated body and the bottom of the biasing member in uncompressed form surrounds the cannula and is vertically displaceable.

2. The pipette assembly of claim 1, wherein the biasing member is temporarily or permanently attached to the pipette assembly.

3. The pipette assembly of claim 1, wherein the biasing member comprises a helical spring.

4. The pipette assembly of claim 3, wherein the helical spring comprises stainless steel.

5. The pipette assembly of claim 1, wherein the biasing member further comprises a restraining component on the bottom end thereof, which modifies the size of the bottom end of the biasing member.

6. The pipette assembly of claim 5, wherein the restraining component comprises a metal washer.

7. A liquid handling instrument for dispensing liquid samples, comprising a moveable liquid handling arm comprising at least one pipette assembly and a controller to which the liquid handling arm is electrically connected, wherein the at least one pipette assembly comprises an elongated body capable of holding a liquid, wherein the elongated body comprises a proximal end for input of the liquid and an opposing distal end in fluid communication with a cannula for dispensing of the liquid into a container, further comprising a biasing member surrounding and associated with at least a portion of the pipette assembly, wherein the biasing member is arranged such that the top of the biasing member is vertically aligned with or below the distal end of the elongated body and the bottom of the biasing member in uncompressed form surrounds the cannula and is vertically displaceable.

8. The liquid handling instrument of claim 7, wherein the biasing member is attached to the pipette assembly.

9. The liquid handling instrument of claim 7, wherein the biasing member comprises a helical spring.

10. The liquid handling instrument of claim 9, wherein the helical spring comprises stainless steel.

11. The liquid handling instrument of claim 7, wherein the biasing member further comprises a restraining component on the bottom end thereof, which modifies the size of the bottom end of the biasing member.

12. The liquid handling instrument of claim 11, wherein the restraining component comprises a metal washer.

13. A method for dispensing a liquid into a container comprising:

providing a moveable liquid handling arm comprising at least one pipette assembly and a controller to which the liquid handling arm is electrically connected, wherein the at least one pipette assembly comprises an elongated body capable of holding a liquid, wherein the elongated body comprises a proximal end for input of the liquid and an opposing distal end in fluid communication with a cannula for dispensing of the liquid into a container, further comprising a biasing member surrounding and associated with at least a portion of the pipette assembly, wherein the biasing member is arranged such that the top of the biasing member is vertically aligned with or below the distal end of the elongated body and the bottom of the biasing member in uncompressed form surrounds the cannula and is vertically displaceable;

providing one or more containers to be filled;

positioning the moveable liquid handling arm horizontally such that one container is vertically below each pipette assembly;

lowering the pipette assembly vertically such that the cannula of the pipette assembly is within the container, wherein the biasing member engages the top of the container and is compressed;

dispensing the liquid into the container; and withdrawing the pipette assembly from the container, wherein the biasing member prevents the container from being vertically displaced during upwards withdrawal of the pipette assembly from the container.

14. The method of claim 13, wherein the biasing member is temporarily or permanently attached to the pipette assembly.

15. The method of claim 13, wherein the biasing member comprises a helical spring.

16. The method of claim 15, wherein the helical spring comprises stainless steel.

17. The method of claim 13, wherein the containers contain a solid or semi-solid material and the biasing member has a compression force that is at least that required for the cannula to penetrate said solid or semi-solid material.

18. The method of claim 17, wherein the solid or semi-solid material comprises a fibrous material.

19. The method of claim 17, wherein the solid or semi-solid material comprises cellulose acetate.

20. The method of claim 13, wherein the biasing member further comprises a restraining component on the bottom end thereof, which modifies the size of the bottom end of the biasing member.

21. The method of claim 20, wherein the restraining component comprises a metal washer.

22. The method of claim 13, wherein the containers are in the form of cartridges for electronic smoking articles.

23. The method of claim 22, wherein the cartridges comprise fibrous reservoirs.

24. The method of claim 22, wherein the liquid comprises an aerosol precursor composition.

25. A method for dispensing an aerosol precursor composition into a cartridge for an electronic smoking article comprising a fibrous reservoir, comprising:

providing a moveable liquid handling arm comprising at least one pipette assembly and a controller to which the liquid handling arm is electrically connected, wherein the at least one pipette assembly comprises a pipette assembly comprising an elongated body capable of holding a liquid, wherein the elongated body comprises a proximal end for input of the liquid and an opposing distal end in fluid communication with a cannula for dispensing of the liquid into the cartridge, further comprising a biasing member surrounding and associated with at least a portion of the pipette assembly, wherein the biasing member is arranged such that the top of the biasing member is vertically aligned with or below the distal end of the elongated body and the bottom of the biasing member in uncompressed form surrounds the cannula and is vertically displaceable;

providing one or more cartridges to be filled;

positioning the moveable liquid handling arm horizontally such that one cartridge is vertically below each pipette assembly;

lowering the pipette assembly vertically such that the cannula of the pipette assembly contacts the fibrous reservoir within the cartridge, wherein the biasing member engages the top of the cartridge and is compressed;

dispensing the liquid into the cartridge; and withdrawing the pipette assembly from the cartridge, wherein the biasing member prevents the cartridge from being vertically displaced during upwards withdrawal of the pipette assembly from the cartridge.

26. The method of claim 25, further comprising tilting the cartridge prior to the dispensing step such that the cartridge is at an angle of between about 5 and 45 degrees with respect to the vertical plane.

27. The method of claim 25, wherein, during the dispensing step, the cannula is in contact with one or both of the fibrous reservoir and the cartridge.

28. The method of claim 25, wherein the fibrous reservoir comprises cellulose acetate.

29. The method of claim 25, wherein the biasing member is temporarily or permanently attached to the pipette assembly.

30. The method of claim 25, wherein the biasing member comprises a helical spring.

31. The method of claim 30, wherein the helical spring comprises stainless steel.

32. The method of claim 25, wherein the biasing member further comprises a restraining component on the bottom end thereof, which modifies the size of the bottom end of the biasing member.

33. The method of claim 32, wherein the restraining component comprises a metal washer.

* * * * *